United States Patent
Vukmirovic et al.

(10) Patent No.: US 7,534,870 B2
(45) Date of Patent: *May 19, 2009

(54) STABLE PHARMACEUTICAL COMPOSITION COMPRISING ERYTHROPOIETIN

(75) Inventors: Andreja Vukmirovic, Ljubljana (SI); Tanja Rozman Peterka, Celje (SI); Jelka Svetek, Ljubljana (SI); Alenka Paris, Ljubljana (SI)

(73) Assignee: Lek Pharmaceuticals d.d., Ljubljana (SI)

(*) Notice: Subject to any disclaimer, the term of this patent is extended or adjusted under 35 U.S.C. 154(b) by 161 days.

This patent is subject to a terminal disclaimer.

(21) Appl. No.: 10/521,298

(22) PCT Filed: Jul. 14, 2003

(86) PCT No.: PCT/SI03/00023

§ 371 (c)(1), (2), (4) Date: May 24, 2005

(87) PCT Pub. No.: WO2004/006958

PCT Pub. Date: Jan. 22, 2004

(65) Prior Publication Data

US 2005/0202091 A1    Sep. 15, 2005

(30) Foreign Application Priority Data

Jul. 17, 2002 (SI) .............................. P-200200178

(51) Int. Cl.
*C12P 21/08* (2006.01)

(52) U.S. Cl. .................. 530/388.23; 424/1.41; 435/335

(58) Field of Classification Search ....................... None
See application file for complete search history.

(56) References Cited

U.S. PATENT DOCUMENTS 5,656,289 A    8/1997   Cho et al.
5,968,899 A    10/1999  Sekine et al.

FOREIGN PATENT DOCUMENTS

| EP | 0 178 576 | 4/1986 |
| WO | 00/07627 | 2/2000 |
| WO | WO 01/87329 | * 11/2001 |

OTHER PUBLICATIONS

[Retrived from] http://www.askoxford.com/concise_oed/substantially?view=uk, 1 page, 2008, [retrieved on Apr. 16, 2008].*

* cited by examiner

*Primary Examiner*—Andrew D Kosar
*Assistant Examiner*—Satyanarayana R Gudibande
(74) *Attorney, Agent, or Firm*—Luedeka, Neely & Graham, P.C.

(57) ABSTRACT

The present invention provides a new stable pharmaceutical composition of erythropoietin (EPO) that is stabilized with a combination of a poloxamer polyol and a polyhydric alcohol.

18 Claims, 7 Drawing Sheets

STABLE PHARMACEUTICAL COMPOSITION COMPRISING ERYTHROPOIETIN

FIELD OF THE INVENTION

The present invention relates to a new stable pharmaceutical composition which comprises erythropoietin (EPO).

EPO is a glycoprotein hormone which regulates the formation of erythrocytes in mammals. It acts as growth and/or differential factor to the erythroid progenitor cells in bone marrow and causes their proliferation and differentiation to erythrocytes.

BACKGROUND OF THE INVENTION

Naturally occurring human EPO is produced by the kidney and is the humoral plasma factor which stimulates red blood cell production. It stimulates the division and differentiation of committed erythroid progenitors in the bone marrow. (Goldwasseret et al., *J. Biol. Chem.*, 249, 4202-4211, 1974, Sherwoodet et al., *Endocrinology*, 103, 866-870, 1978). It is produced in adult kidneys (Sherwood et al., Endocrinology, 103, 866-870, 1978) and in fetal liver (Zanjani et Al., J. Lab. Clin. Med., 89, 640-644, 1977).

The administration of a pharmaceutical composition of EPO to the organism stimulates and/or accelerates the production of erythrocytes. The pharmaceutical composition of EPO is used in the treatment of chronic renal failure, anemia secondary to chemotherapy treatment in cancer and anemia associated with zidovudine treatment of human immunodeficiency virus infection and in the treatment of other kinds of anemias (Danna et al., Erythropoietin in Clinical Applications—An International Perspective. New York, N.Y.: Marcel Dekker; 301-324, 1990; Eschbach in sod., *N. England J. of Med.*, 316, 2, 73-78, 1987; Krane, *Henry Ford Hosp. Med. J.*, 31,3,177-181, 1983).

Recombinant EPO, which is the product of expression of the human EPO gene in mammalian cells is used in pharmaceutical compositions of EPO (EP 148605, EP 205564, EP255231). Also some EPO analogs and derivatives are described in the art: EP640619, EP 668351, WO 9412650, EP1064951, WO 0232957, WO 9533057, U.S. Pat. No. 5,916,773, WO 09902710, U.S. Pat. No. 5,580,853, U.S. Pat. No. 5,747,446, U.S. Pat. No. 5,919,758 and U.S. Pat. No. 6,107,272.

Pharmaceutical compositions of EPO, which comprise human serum albumin, are described in: EP 178665, EP 178576, U.S. Pat. No. 5,661,125, WO 0061169. Human serum albumin can cause allergic reactions (Stafford C T et al., *Ann Allergy*, 61(2), 85-88, 1988). Furthermore there exist a risk of infection with viruses when a pharmaceutical composition comprises human blood products. Therefore pharmaceutical formulations of EPO that are stable and are free of human blood products, such as albumin are needed.

EP 306824, EP 607156, EP 528313 and EP 528314 describe pharmaceutical compositions, in which urea is used as an EPO stabilising agent.

EP306824, EP 178665, GB 2171304, EP 528314, EP 528313 and EP 1002547 describe lyophilized formulations of EPO.

U.S. Pat. No. 5,376,632 describes a pharmaceutical formulations, in which alpha and beta cyclodextrines are used.

EP 607156, EP 528313 in EP178665 describe aqueous pharmaceutical compositions of EPO, which comprise antimicrobial preservatives such as benzyl alcohol, parabens, phenols, and mixtures thereof.

EP 909564, EP 528314, EP 430200 and WO 0061169 describe the use of aminoacids and/or the combination of aminoacids and non-ionic detergents as stabilising agents.

WO 0187329 describes different pharmaceutical compositions of pegylated EPO analog. The described pharmaceutical compositions are essentially based on the use of sulfate buffer.

Some of the pharmaceutical compositions of EPO described in: RU 2128517, WO0061169, EP 528313, EP 607156, EP 528314, EP 178665, are prepared in citrate buffer.

SUMMARY OF THE INVENTION

The object of the invention is to provide a pharmaceutical composition comprising EPO which is capable of beneficially stabilising EPO.

The present invention provides a new stable pharmaceutical composition comprising EPO in accordance with claim 1. Preferred embodiments are set forth in the sub-claims. The present invention also provides a process according to claim 21, and a use according to claim 22.

The pharmaceutical composition is formulated with a pharmaceutically acceptable pH buffering system and comprises a combination of two stabilizers: a poloxamer polyol (copolymer of ethylene oxide and propylene oxide) and a polyhydric alcohol.

The stabilisation of EPO is achieved while the composition of the invention is preferably free of additives which are derived from human or animal origin other than EPO (e.g. serum proteins). The pharmaceutical composition optionally further comprises an isotonifying agent and/or one or more pharmaceutically acceptable excipients. The pharmaceutical composition of the present invention is suitable for use in human and veterinary medicine and is pharmaceutically acceptable in a suitable administration form, especially for parenteral application, e.g. intramuscular, subcutaneous and/or intravenous application. In a particularly preferred embodiment, the pharmaceutical composition of the present invention is in a liquid, more preferably in an aqueous form.

DESCRIPTION OF THE INVENTION AND OF PREFERRED EMBODIMENTS

Figure 1:
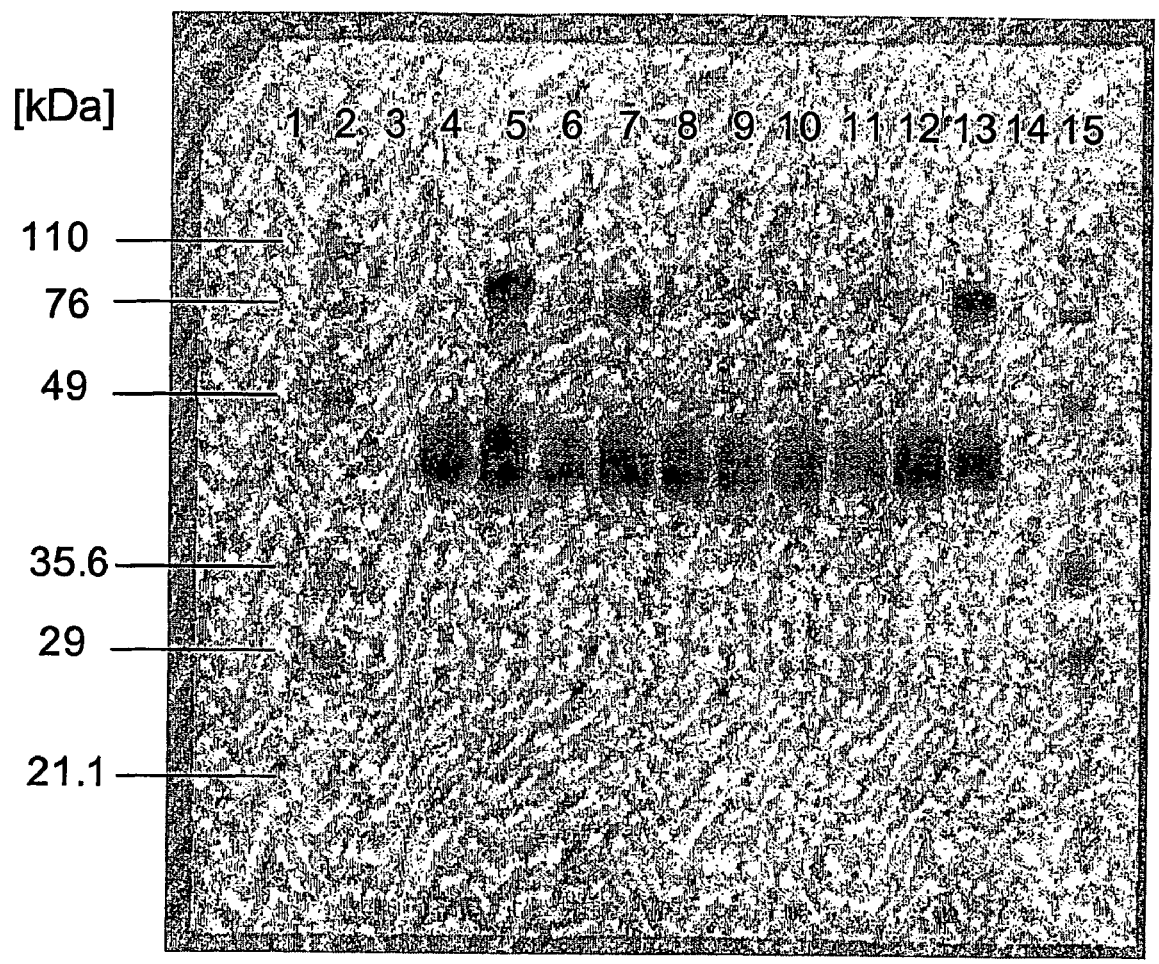
FIG. 1 shows SDS-PAGE analysis of inventive and reference samples comprising EPO after having been stored at 40° C. (±2° C.) for 1 month.

It was surprisingly found that a pharmaceutical composition which comprises a non-ionic surface agent poloxamer polyol (copolymer of ethylene oxide and propylene oxide) and polyhydric alcohol and which is preferably free of additives other than EPO derived from human and/or animal origin, beneficially stabilises EPO.

The present invention provides the pharmaceutical composition of EPO comprising:
  a. a therapeutically effective amount of EPO,
  b. a pharmaceutically acceptable pH buffering system,
  c. a poloxamer polyol, and
  d. a polyhydric alcohol.

The present invention also provides the pharmaceutical composition of EPO which optionally further comprises in addition to components a-d:
  e. an isotonifying agent and/or
  f. one or more of other pharmaceutically acceptable excipients.

The composition of the invention is preferably free of additives derived from human or animal origin.

The term 'erythropoietin (EPO)' refers to a protein with the in vivo biological activity of causing bone marrow cells to increase production of reticulocytes and red blood cells and is selected from the group consisting of human EPO and derivatives and analogs which are defined below.

The term 'therapeutically effective amount of EPO' refers to the amount of EPO which enables a therapeutical effect of EPO.

The term 'stabiliser' refers to a pharmaceutical acceptable excipient, which has a stabilising effect on EPO.

The term 'EPO stability' refers to the maintenance of EPO content and to the maintenance of EPO biological activity. The EPO stability may be influenced inter alia by the following processes: adsorption of EPO to the container walls, denaturation or degradation of EPO and aggregate formation of e.g. EPO dimers and/or EPO multimers and/or similar molecules with higher molecular weight. These processes occur due to exposing of the samples to different conditions, e.g. higher temperature, inappropriate containers, use of wrong stabilisers of EPO, sunshine, inappropriate way of storing and/or inappropriate isolation procedure.

The term "free of additives derived from human and/or animal origin" refers to the condition that additives which originate from human and/or animal and which are different from EPO, such as serum albumins like HSA or BSA, are not intentionally added to the composition, or if originally present in an EPO preparation have been separated or reduced during the purification and/or isolation of EPO to an unavoidable level of traces, preferably to a level that is typically undetectable by standard analytical methods.

It has been surprisingly found that formulating EPO in the composition of the invention improves its stability at temperatures above refrigerator temperature (e.g. 2-8° C.), especially at room temperature (i.e. below 25° C.) and even at higher temperatures (e.g. 40° C.). This means that the composition can be stored without cooling for a prolonged period of time (more than 10 weeks at room temperature), without loosing significant amounts of activity and without significant degradation.

Although not being restricted in this way, the pharmaceutical composition of the present invention may preferably consist only of the aforementioned constituents a.-d., or optionally a.-e., a.-d. plus f., or a.-f.

In some pharmaceutical compositions known from the prior art the non-ionic detergents like Polysorbate 80 are used as stabilisers of EPO. The use of a poloxamer polyol (copolymer of ethylene oxide and propylene oxide) and/or polyhydric alcohol is advantageous over the use of polysorbates because gel filtration can be used as analytical method for the determination of EPO dimers, EPO multimers and related substances with higher molecular mass which result from the aggregation of EPO molecules. The polysorbates are eluted at the same time as are EPO dimers. Therefore the gel filtration can not be used as a detection method for EPO dimers for the pharmaceutical compositions which comprise polysorbates. The use of a combination of poloxamer polyol (copolymer of ethylene oxide and propylene oxide) and polyhydric alcohol therefore contributes to an easier way of proving of EPO stability, to an increased safety and an easier control of the quality of pharmaceutical composition of EPO.

The pharmaceutical composition of the present invention is preferably a liquid and particularly an aqueous pharmaceutical composition. Such a liquid composition can be directly used for parenteral application such as subcutaneous, intravenous or intramuscular application without reconstitution, diluting or additional preparation steps which could lead to a lowering or even a loss of EPO biological activity, and also can contribute to avoid additional technical problems occurring at the time of application. The use of a liquid pharmaceutical composition is therefore more practical as the use of lyophilized formulations. Liquid and particularly aqueous formulations of EPO are generally preferred over lyophilized formulation for preparing the clinical formulation of EPO, because the reconstitution process of lyophilized compositions is time consuming, poses risks of improper handling of the protein formulation, or may be reconstituted improperly, and certain additives such as stabilisers are usually required to retain sufficient activity of the drug.

The pharmaceutical composition of the present invention is most preferably free of additives derived from human or animal origin like human serum proteins which, despite blood screening, pose a risk of infection with a transmissible agent. Further, although recombinant EPO is generally well tolerated, occasional skin rashes and urticaria have been observed suggesting allergic hypersensitivity to some components of the EPO formulation, likely human serum albumin.

The pharmaceutical composition of the present invention can be suitably prepared in isotonic solution and is expected to be pharmaceutically acceptable and causing no side effects like allergic hypersensitivity.

The pharmaceutical composition of the present invention can be used for all forms of EPO, comprising EPO alfa, EPO beta, EPO omega and other EPO preparations having different isoform profiles, as well as for specific EPO isoforms, EPO muteins, EPO fragments, EPO analogs such as EPO dimers, NESP (hyperglycosilated analog of recombinant human EPO), gene activated EPO, pegylated EPO, hybrid molecules with EPO, EPO fragments, fusion protein (oligomers and multimers) with EPO, EPO with modified glycosilation profiles regardless of the biological activity of EPO and further regardless of the method of synthesis or manufacture thereof, which method may include but is not limited to the isolation of naturally occurring EPO and recombinant EPO whether produced from cDNA or genomic DNA, synthetic, transgenic and gene activated methods.

The pharmaceutical composition of the present invention may comprise from 500 to 100000 units or more EPO per dose (1 IU corresponds to about 10 nanograms of recombinant EPO). In general it is contemplated that an effective amount will be from 1 to 500 IU/kg body weight and more preferably from 50 to 300 IU/kg body weight, especially when EPO is given subcutaneously. The effective amount will further depend on the species and size of the subject being treated, the particular condition or disease being treated and its severity and the route of administration. In preferred embodiments, the pharmaceutical quantity is formulated to provide a quantity per dose selected from the group consisting of about 1000 IU, about 2000 IU, about 3000 IU, about 4000 IU, about 10000 IU, about 20000 IU, about 25000 IU, about 40000 IU, about 50000 IU, about 60000 IU, and about 100000 IU.

The pharmaceutical composition of the present invention can be filled in ampoules, injection syringes, multi dose cartridges and vials. These enable the application in volumes in the suitable range from 0.2 to 20 ml per dose.

The preferred pH range for the solutions is from about 6 and to about 8 with a range from about 6.8 to about 7.5 being more preferred and a pH of about 7.0 being most preferred. The use of a phosphate buffer system, especially sodium phosphate dibasic and sodium phosphate monobasic such as $NaH_2PO_4 \times 2H_2O/Na_2HPO_4 \times 2H_2O$, is preferred. Other suitable buffer systems to maintain the desired pH range of about 6 to about 8 include, but are not limited to, sodium citrate/citric acid, sodium acetate/acetic acid, and any other pharmaceutically acceptable pH buffering agent known in the art. Citrate buffer may cause pain at the injection site. Therefore the phosphate buffer is more preferable for the parenteral application.

The concentration of pH buffering system, especially the phosphate buffer, depends on the desired pH of the formulation. The preferred concentration is in the range from 10 to 50 mM, more preferred from 15 to 35 mM, most preferred from 15 to 25 mM. There may be added a pH-adjusting agent such as, but not limited to HCl, NaOH, citric acid or sodium citrate.

The pharmaceutical composition of the present invention comprises a combination of a non ionic surface active substance poloxamer polyol and a polyhydric alcohol. Among poloxamer polyols Pluronic F68 is used preferably. The preferred concentration of poloxamer polyol comprises the range to 1% (m/v), more preferably between 0.05% (m/v) and 0.5% (m/v), the most preferably 0.1% (m/v). The polihydyric alcohol is selected from the group comprising glycerol, sorbitol, mannitol, xylitol and others. Among them preferably sorbitol and glycerol are used, most preferably glycerol is used. The preferred concentration of a polyhydric alcohol comprises the range between 0.1% (m/v) and 10% (m/v), more preferred between 0.5% (m/v) and 6% (m/v), the most preferred from 1% to 3% (m/v).

The pharmaceutical composition of the present invention optionally further comprises an agent capable of rendering the formulations of the present invention isoosmotic with human blood. Typical suitable isotonifying agents are well known in the art, and include, but are not limited to, agents selected from the group consisting of mannitol, glycine, glucose and inorganic salts such as NaCl, $CaCl_2$. Use of NaCl as an isotonifying agent is preferred in the formulations of the present invention.

Although the formulation with a combination of a poloxamer polyol (copolymer of ethylene oxide and propylene oxide) and a polyhydric alcohol as the EPO stabilizers is preferred as mentioned above, the pharmaceutical composition of the present invention may optionally comprise more than one type of stabiliser besides the aforementioned components a., b. and optionally e. and f., if desired.

This additional EPO stabiliser is preferably selected from the group which comprises surface active agents such as glycol and glycerol esters, macrogol esters and ethers, sorbitan derivatives/polysorbates (e.g. Polysorbate 20, Polysorbate 80) and polymers (PVP). Among them, the polymers in the concentration to 1% are preferred. The most preferred is polymer PVP K12 in the concentration of 0.5%.

The pharmaceutical composition of the present invention may optionally further comprise one or more pharmaceutically acceptable excipients. Suitable pharmaceutically acceptable excipients include polyethylenglycol, hydroxypropylcellulose, methylcellulose, and amino acids such as glycine, L-isoleucine, L-leucine, L-glutamic acid, L-2-phenylalanine, L-threonin.

The composition of the present invention can be used for the preparation of medicaments for the treatment and/or prevention of diseases that are indicated for EPO. Examples of medical uses include a variety of therapies where stimulation of red blood cell proliferation (RBC) is desired, where there exists an endogenous hormone deficiency, where blood is lost or where a patient has indications of anemia, or has hyporesponsiveness of the bone marrow to the endogenous hormone. These medical indications are for example anemia of malignant disease (i.e. any type of solid cancer, or hematological cancer including leukemia, lymphoma and multiple myeloma), anemia resulting from a chemotherapeutic/radiation treatment of a malignant disease, anemia of chronic disease including for example autoimmune diseases such as rheumatoid arthritis and hepatitis, anemia in AIDS patients, especially those treated with AZT, anemia of prematurity, anemia associated with (chronic) renal failure, anemia of thalasemia, autoimmune hemolytic anemia, aplastic anemia, and anemia associated with surgery (e.g. for improving preoperative blood donation for autotransfusion to stimulate and increase in hemoglobin levels to counter substantial blood loss or to increase erythropoiesis in subjects undergoing bone marrow transplantation), the treatment of fatigue, pain, chronic heart failure, dysrythmia or dementia, preoperatively use to reduce the need for allogenic blood transfusion in non-vascular and non-cardiac surgery and other indications indicated for EPO.

The following examples illustrate the present invention without, however, limiting the same thereto.

EXAMPLES

Analytical Methods

The following analytical methods were used for the analysis of the pharmaceutical composition of the present invention: SDS-PAGE with immunodetection, size exclusion chromatography (SEC), EPO-ELISA and in vivo biological activity assay on mice.

SDS-PAGE with immunodetection: The loading samples were prepared in the loading buffer free of reducing agent. The vertical SDS-PAGE was used: gel NuPAGE Bis-Tris 12%, 8×8 cm, thickness 1.0 mm, 15 lanes (Invitrogen) in MOPS SDS electrophoresis buffer (Invitrogen). Electrophoresis ran 1 hour at constant voltage of 200 V. After the electro transfer from the gel to the nitro-cellulose membrane the immunodetection was performed in two steps. In the first one the primary antibodies (anti-huEPO, mouse, monoclonal) were used. In the second step the secondary antibodies (anti-mouse IgG, rabbit, polyclonal) conjugated to horseradish peroxidase was used. The addition of the peroxidase substrate triggers enzyme reaction to form a blue coloured complex.

EPO-ELISA: System EPO-ELISA Quantikine IVD, R&D Systems, is based on the double-antibody sandwich method. Microplate wells, precoated with monoclonal (murine) antibody specific for EPO are incubated with specimen or standard. EPO binds to the immobilized antibody on the plate. After removing specimen or standard, wells are incubated with an anti-EPO polyclonal (rabbit) antibody conjugated to horseradish peroxidase. During the second incubation, the antibody-enzyme conjugate binds to the immobilized EPO. A chromogen is added to the wells and is oxidized by the enzyme reaction to form a blue coloured complex. The amount of colour generated is directly proportional to the amount of conjugate bound to the EPO antibody complex, which, in turn, is directly proportional to the amount of EPO in the specimen or standard.

SEC: SEC was used to determine the proportion of EPO dimers and related substances of higher molecular mass in the samples from FP1 to FP8 with the EPO content from 2000 IU/ml to 10000 IU/ml. The limit assay following the protocols of European Pharmacopoeia was used (European Pharmacopoeia 2002, 4$^{th}$ edition, Erythropoietin concentrated solution).

In vivo Biological Activity:

The protocol for in vivo determination of biological activity on hypoxic mice described in Eur. Ph was used. The estimation of biologic activity was performed under the protocols from Eur. Ph as well (Eur. Pharmacopoeia—1997; Statistical Analysis of Results of Biological Assays and Tests; The parallel-line model). Under the demands of Eur. Ph the estimated value of biologic activity should be in the range between 80% and 120% of the marked activity. The aim of the method is to reach the range between 80% and 120% regarding the content (value) of the EPO injected (10000 IU/ml) and the results obtained represent the estimation of biological activity and not its precise value. The confidential limit should be in the range between 64% and 156% of the marked activity.

The conditions for testing the stability of pharmaceutical compositions of EPO

| HL-reference | 2 to 8° C., refrigerator |
|---|---|
| 40 | 40° C. ± 2° C., 75% ± 5% relative humidity, climatic chamber |
| 25 | 25° C. ± 2° C., 60% ± 5% relative humidity, climatic chamber |

Example 1

Stability Tests

The following compositions of the formulations FP1 through FP8 were prepared:

FP1: polysorbate 80 (0.03% (weighVvolume (w/v))), glycine (0.5% (w/v)), phosphate buffer 20 (mmol/l), NaCl (100 mmoll/l)

FP2: glycine (0.5% (w/v)), glycerol (1.4% (w/v)), phosphate buffer (32 mmol/l)

FP3: glycine (0.5% (w/v)), Pluronic F68 (0.1% (w/v)), phosphate buffer (20 mmol/l), NaCl (90.6 mmol/l)

FP4: sorbitol (4.5% (w/v)), Pluronic F68 (0.1% (w/v)), phosphate buffer (20 mmol/l)

FP5: dextran 70 (1% (w/v)), NaCl (123 mmol/l), phosphate buffer (20 mmol/l)

FP6: glycerol (2% (w/v)), Pluronic F 68 (0.1% (w/v)), NaCl (17.1 mmol/l) phosphate buffer (20 mmol/l)

FP7: glycerol (2% (w/v)), PVP K12 (0.5% (w/v)), phosphate buffer (20 mmol/l).

FP8: PVP K12 (0.5% (w/v)), NaCl (123 mmol/l), phosphate buffer (20 mmol/l)

The content of EPO in the formulations is set to 2000 IU/ml or 10000 IU/ml, as described below.

Samples from FP1 to FP8, with a respective EPO content of 10000 IU/ml, were stored at 40° C. (±2° C.) for 1 month (40). EPO bulk in phosphate buffer stored at 40° C. (±2° C.) for 1 month was taken as a positive control (PK) for the determination of the content of EPO dimers. The samples were subjected to SDS-PAGE; 0.4 µg was loaded in each lane. FIG. 1 shows the results.

| Legend of FIG. 1: | |
|---|---|
| Lane | Sample |
| 1 | empty lane |
| 2 | prestained SDS-PAGE MW standards, low range, Bio-Rad, 4 µl load |
| 3 | empty lane |
| 4 | EPO-BRP (EPO standard of the European Pharmacopoeia) |
| 5 | FP1 40 |
| 6 | FP2 40 |
| 7 | FP3 40 |
| 8 | FP4 40 |
| 9 | FP5 40 |
| 10 | FP6 40 |
| 11 | FP7 40 |
| 12 | FP8 40 |
| 13 | PK |
| 14 | empty lane |
| 15 | prestained SDS-PAGE MW standards, low range, Bio-Rad, 4 µl load |

Figure 2:
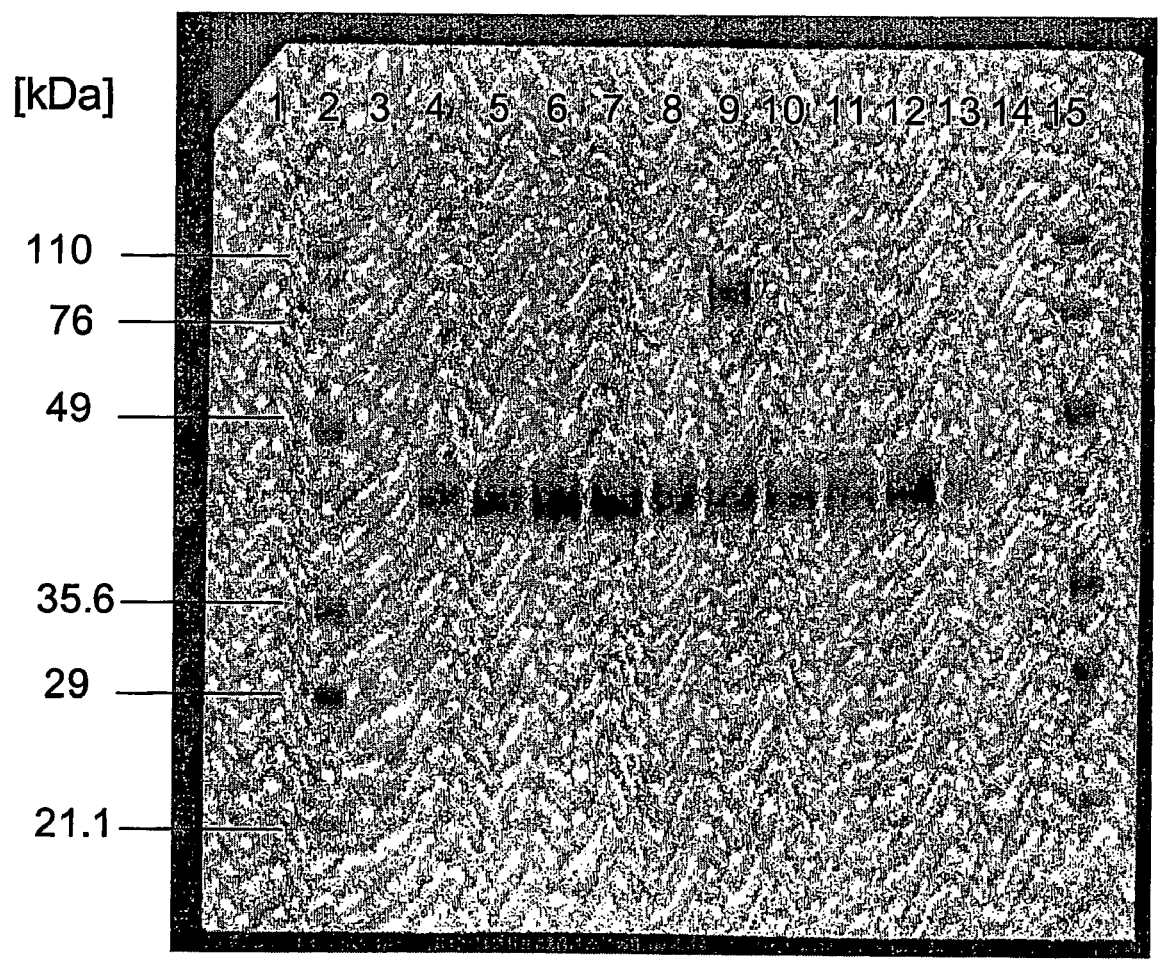
FIG. 2 shows SDS-PAGE analysis of reference samples comprising EPO when being stored in the refrigerator for 1 month in comparison with being stored at 40° C. (±2° C.) for 1 month.

FIG. 2 shows the SDS-PAGE of the samples from FP1 to FP4, with a respective EPO content of 10000 IU/ml, stored in the refrigerator (HL) and stored at 40° C. (±2° C.) 1 month (40). EPO bulk in phosphate buffer stored at 40° C. (±2° C.) 1 month was taken as a positive control (PK) for the determination of the content of EPO dimers. 0.4 µg was loaded in each lane.

| Legend of FIG. 2: | |
|---|---|
| Lane | Sample |
| 1 | empty lane |
| 2 | prestained SDS-PAGE MW standards, low range, Bio-Rad, 4 µl load |
| 3 | empty lane |
| 4 | EPO-BRP (EPO standard of the European Pharmacopoeia) |
| 5 | FP1 HL |
| 6 | FP2 HL |
| 7 | FP3 HL |
| 8 | FP4 HL |
| 9 | FP1 40 |
| 10 | FP2 40 |
| 11 | FP3 40 |
| 12 | FP4 40 |
| 13 | PK |
| 14 | empty lane |
| 15 | prestained SDS-PAGE MW standards, low range, Bio-Rad, 4 µl load |

Figure 3:
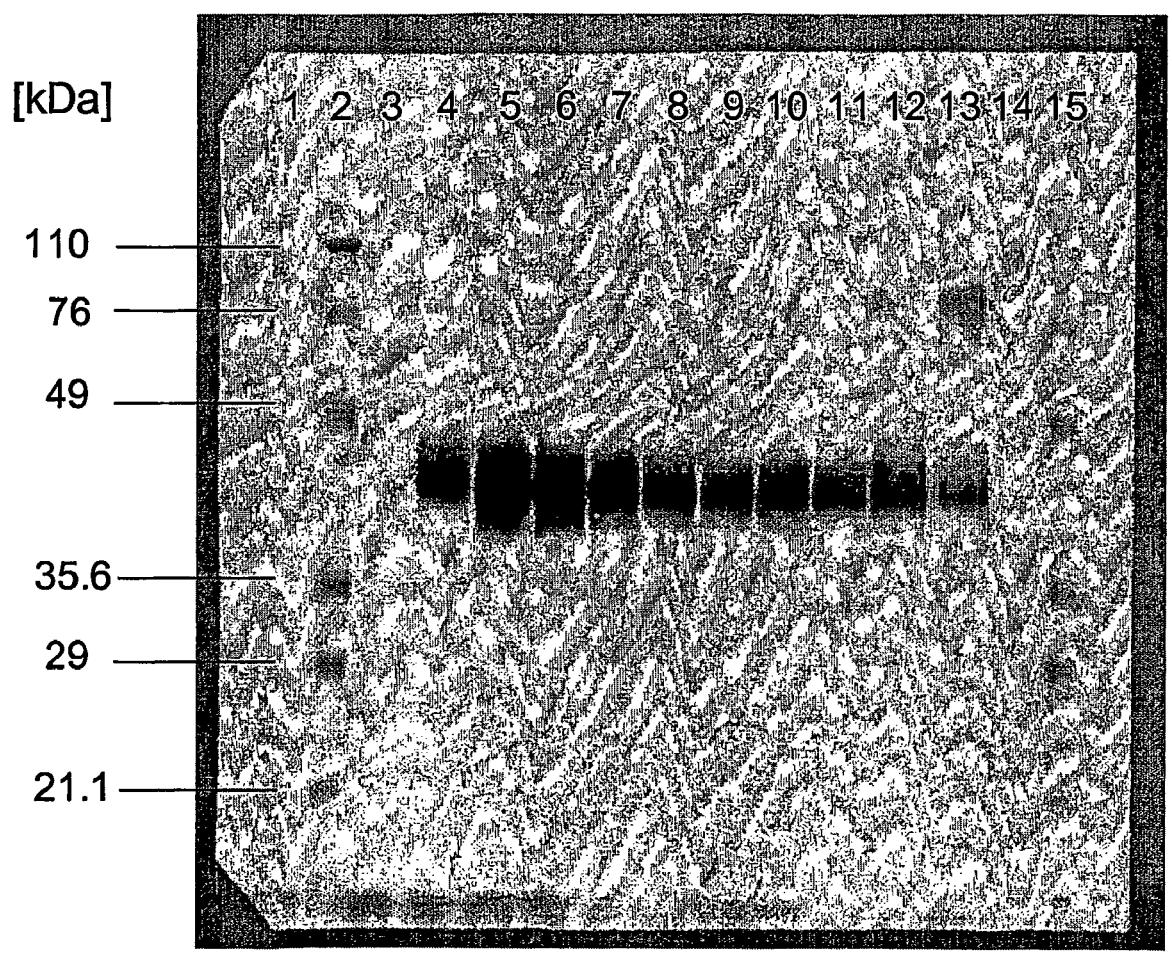
FIG. 3 shows SDS-PAGE analysis of the inventive and reference samples comprising EPO when being stored in the refrigerator for 1 month in comparison with being stored at 40° C. (±2° C.) for 1 month.

FIG. 3 shows the SDS-PAGE of the samples from FP5 to FP8, with a respective EPO content of 10000 IU/ml, stored in the refrigerator (HL) and stored at 40° C. (±2° C.) 1 month (40). EPO bulk in phosphate buffer stored at 40° C. (±2° C.) 1 month was taken as a positive control (PK) for the determination of the content of EPO dimers. 0.4 μg was loaded in each lane.

Legend of FIG. 3:

| Lane | Sample |
|---|---|
| 1 | empty lane |
| 2 | prestained SDS-PAGE MW standards, low range, Bio-Rad, 4 μl load |
| 3 | empty lane |
| 4 | EPO-BRP (EPO standard of the European Pharmacopoeia) |
| 5 | FP5 HL |
| 6 | FP6 HL |
| 7 | FP7 HL |
| 8 | FP8 HL |
| 9 | FP5 40 |
| 10 | FP6 40 |
| 11 | FP7 40 |
| 12 | FP8 40 |
| 13 | PK |
| 14 | empty lane |
| 15 | prestained SDS-PAGE MW standards, low range, Bio-Rad, 4 μl load |

Figure 4:
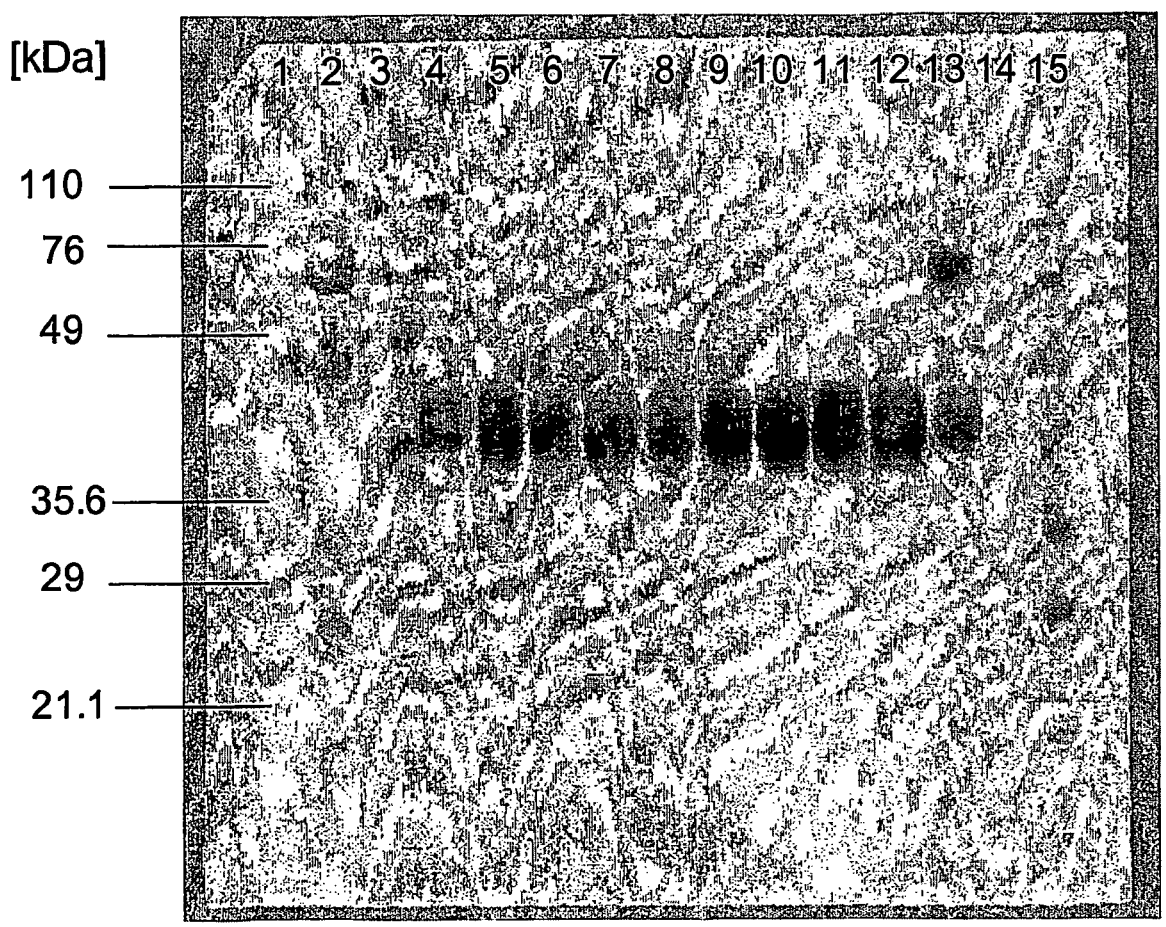
FIG. 4 shows an SDS-PAGE analysis of inventive and reference samples comprising EPO when stored in the refrigerator for 10 weeks.

FIG. 4 shows the SDS-PAGE of the samples from FP1 to FP8, with a respective EPO content of 10000 IU/ml, stored in the refrigerator (HL) 10 weeks. EPO bulk in phosphate buffer stored at 40° C. (±2° C.) 1 month was taken as a positive control (PK) for the determination of the content of EPO dimers. 0.4 μg was loaded in each lane.

Legend of FIG. 4:

| Lane | Sample |
|---|---|
| 1 | empty lane |
| 2 | prestained SDS-PAGE MW standards, low range, Bio-Rad, 4 μl load |
| 3 | empty lane |
| 4 | EPO-BRP (EPO standard of the European Pharmacopoeia) |
| 5 | FP1 HL |
| 6 | FP2 HL |
| 7 | FP3 HL |
| 8 | FP4 HL |
| 9 | FP5 HL |
| 10 | FP6 HL |
| 11 | FP7 HL |
| 12 | FP8 HL |
| 13 | PK |
| 14 | empty lane |
| 15 | prestained SDS-PAGE MW standards, low range, Bio-Rad, 4 μl load |

Figure 5:
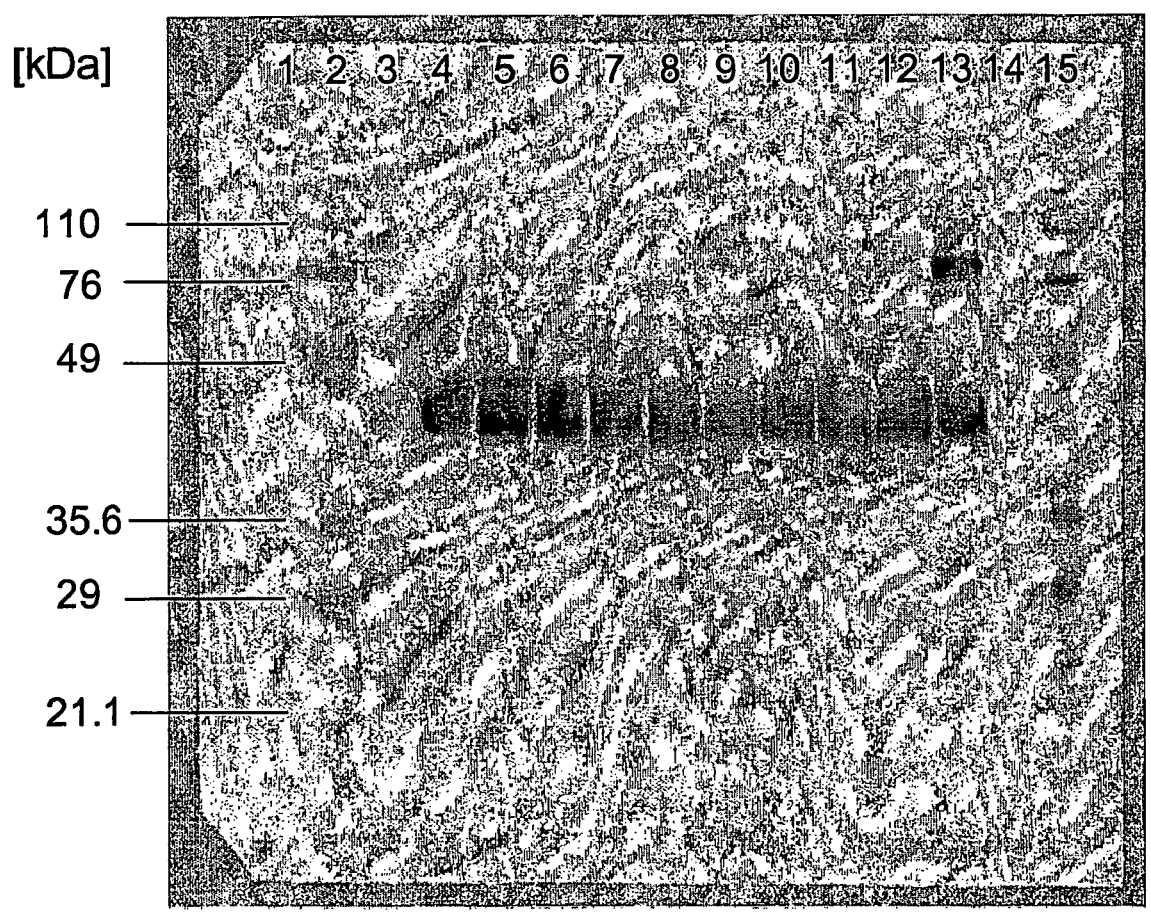
FIG. 5 shows an SDS-PAGE analysis of the inventive and reference samples comprising EPO when being stored at 25° C. (±2° C.) for 10 weeks.

FIG. 5 shows the SDS-PAGE of the samples from FP1 to FP8, with a respective EPO content of 10000 IU/ml, stored at 25° C. (±2° C.) 10 weeks (25). EPO bulk in phosphate buffer stored at 40° C. ('52° C.) 1 month was taken as a positive control (PK) for the determination of the content of EPO dimers. 0.4 μg was loaded in lane.

Legend of FIG. 5:

| Lane | Sample |
|---|---|
| 1 | empty lane |
| 2 | prestained SDS-PAGE MW standards, low range, Bio-Rad, 4 μl load |
| 3 | empty lane |
| 4 | EPO-BRP (EPO standard of the European Pharmacopoeia) |
| 5 | FP1 25 |
| 6 | FP2 25 |
| 7 | FP3 25 |
| 8 | FP4 25 |
| 9 | FP5 25 |
| 10 | FP6 25 |
| 11 | FP7 25 |
| 12 | FP8 25 |
| 13 | PK |
| 14 | empty lane |
| 15 | prestained SDS-PAGE MW standards, low range, Bio-Rad, 4 μl load |

Figure 6:
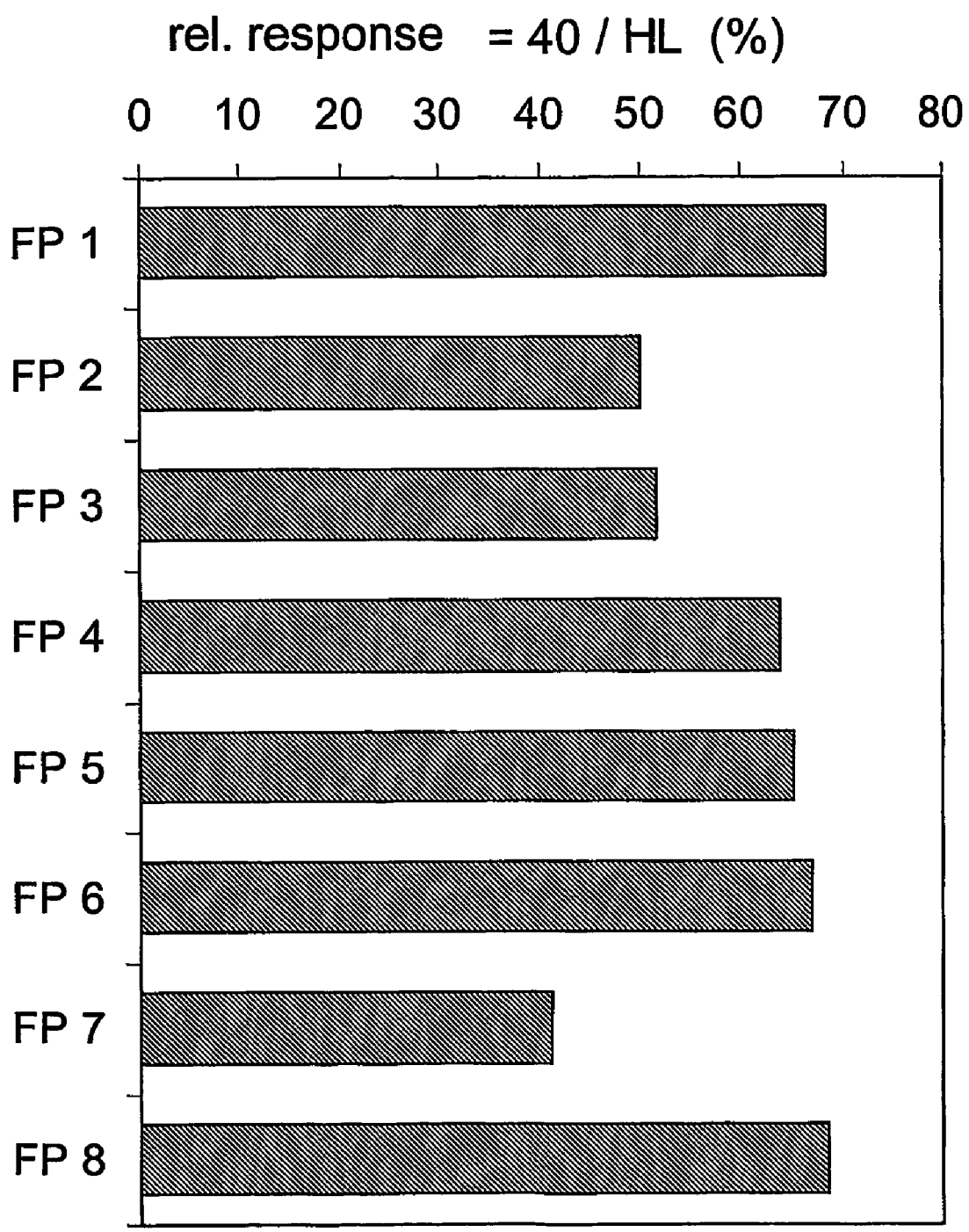
FIG. 6 shows the relative response EPO-ELISA (in %) of inventive and reference samples when stored at 40° C. (±2° C.) for 1 month (40) to the respective samples when stored in the refrigerator for 1 month (HL).

FIG. 6 shows the relative response of EPO-ELISA (in %) of the samples from FP1 to FP8, with a respective EPO content of EPO 10000 IU/ml, stored at 40° C. (±2° C.) for 1 month (40), to the samples from FP1 to FP8, stored in the refrigerator for 1 month (HL).

Figure 7:
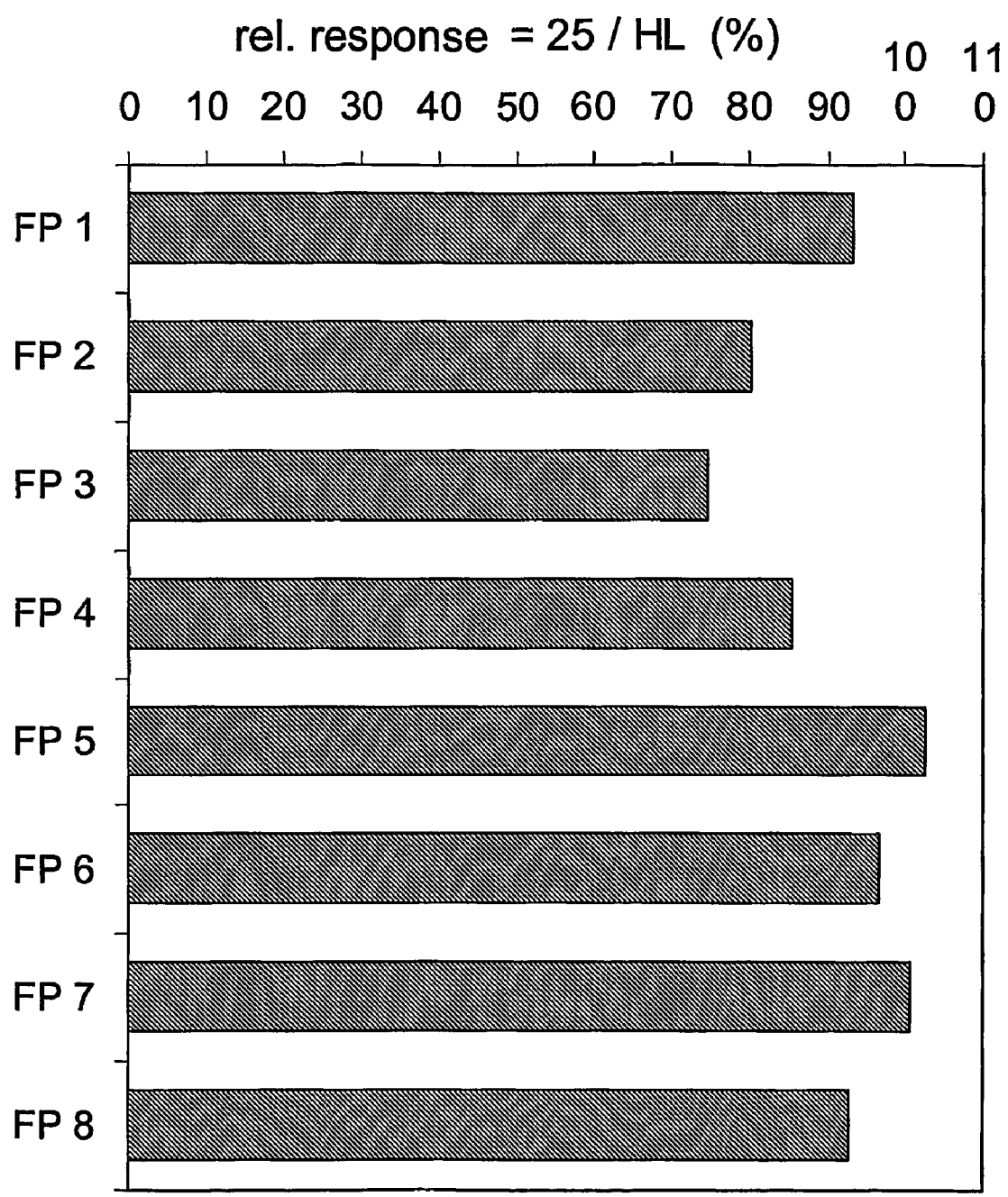
FIG. 7 shows the relative response EPO-ELISA (in %) of inventive and reference samples comprising EPO when stored at 25° C. (±2° C.) for 10 weeks (25) to the respective samples when stored in the refrigerator for 10 weeks (HL).

FIG. 7 shows the relative response of EPO-ELISA (in %) of the samples from FP1 to FP8, with a respective EPO content of EPO 10000 IU/ml, stored at 25° C. (±2° C.) for 10 weeks (25), to the samples from FP1 to FP8, stored in the refrigerator for 10 weeks (HL).

Results of Stabilty Tests:

The SDS-PAGE with immunodetection shows that EPO aggregates, for example EPO dimers and related substances of higher molecular mass, do not occur in the pharmaceutical composition of the present invention (FP6) at room temperature (FIGS. 1-5). At elevated temperatures they are present in small amounts. Comparison of EPO stability at elevated temperature (1 month at 40° C.) of the pharmaceutical composition of the present invention with the pharmaceutical composition FP1, in which the combination of polysorbates and the amino acid glycine is used (FIGS. 1,2,3), shows that EPO dimers are formed in FP1. The formation of EPO dimers is one of crucial factors for EPO stability. It is also possible that EPO aggregates, e.g. EPO dimers and related substances of higher molecular mass measured, cause undesired side effects after the application and non-comfortability of the patient treated with the pharmaceutical composition. It is also possible that these aggregates cause immune response of the organism and the treatment with EPO has to be stopped.

The pharmaceutical composition of the present invention (FP6) in comparison with other prepared pharmaceutical compositions (FP1—FP5, FP7, FP8) at elevated temperature (40° C., 1 month; FIG. 6) shows that the adsorption of EPO to the vials of FP6 is lower or equal when compared to other formulations. At room temperatures the adsorptions are comparable or better (FIG. 7). An increased adsorption to the vials would decrease the EPO stability, and the entire biological activity would be decreased.

Amino acids have been used as stabilising agent of EPO in the formulations described in prior art. But amino acids do not always exhibit a stabilising effect on EPO. In FIGS. 6 and 7 it is seen that the stability at room (25° C. 10 weeks) and elevated temperatures (40° C. 1 month) of pharmaceutical compositions FP2 and FP3 comprising glycine is lower than the stability of pharmaceutical preparations FP4, FP5, FP6 and FP8, which do not contain glycine, and is also lower than FP1 which comprises glycine. High EPO stability can be obtained with the use of right combination of different stabilising agents, but their appropriate composition cannot be predicted. With the pharmaceutical composition of the present invention it was surprisingly found that the combination of a poloxamer polyol (copolymer of ethylene oxide and propylene oxide) and polyhydric alcohol stabilised EPO.

The proportion of EPO dimers and related substances of higher molecular mass measured by SEC was compared with diluted solutions of the samples (at a concentration of 2%). The results of limit assay are presented in Table 1 below:

TABLE 1

| Sample | The estimation of EPO dimer proportions | |
|---|---|---|
| | 40° C. 1 month | 25° C. 10 weeks |
| FP1 (2000 IU/ml) | * | * |
| FP1 (10000 IU/ml) | * | * |
| FP2 (2000 IU/ml) | <2% | <2% |
| FP2 (10000 IU/ml) | >2% | <2% |
| FP3 (2000 IU/ml) | >2% | <2% |
| FP3 (10000 IU/ml) | >2% | <2% |
| FP4 (2000 IU/ml) | <2% | <2% |
| FP4 (10000 IU/ml) | <2% | <2% |
| FP5 (2000 IU/ml) | ** | ** |
| FP5 (10000 IU/ml) | (>2%)** | ** |
| FP6 (2000 IU/ml) | <2% | <2% |
| FP6 (10000 IU/ml) | >2% | <2% |
| FP7 (2000 IU/ml) | <2% | <2% |
| FP7 (10000 IU/ml) | <2% | <2% |
| FP8 (2000 IU/ml) | <2% | <2% |
| FP8 (10000 IU/ml) | <2% | <2% |

*denotes that the determination of the proportion of dimers was not possible due to polysorbates from placebo
**denotes that the determination of the proportion of dimers was not possible due to dextran.

Small amounts of higher molecular mass related substances were also detected in most samples, but were not included in the presentation.

The in vivo biological activity was measured in the sample FP6 with an EPO content of 10000 IU/ml, stored at 25° C. for 10 weeks. The results obtained are presented in Table 2 below:

TABLE 2

| Sample | Estimation of biological activity (80-120%) | Conf. limit (64-156%) |
|---|---|---|
| FP6 | 10111 IU/ml (101%) | 74-106% |

The results show that the estimated biological activity is in the demanded range and corresponds to the demands of Eur. Ph. The confidential limits are also in the demanded range.

Examples 2 and 3

Compositions of Pharmaceutical Compositions of EPO

The compositions of inventive (pharmaceutical compositions presented in) Examples 2 and 3 are set out in Tables 3 and 4, respectively.

TABLE 3

| Sample | Active ingredient | Inactive ingredient |
|---|---|---|
| FP6 (2000) | 2000 IU EPO | $NaH_2PO_4 \times 2H_2O$ 1.164 mg = 0.1164% |
| | | $Na_2HPO_4 \times 2H_2O$ 2.225 mg = 0.2225% |

TABLE 3-continued

| Sample | Active ingredient | Inactive ingredient |
|---|---|---|
| | | NaCl 7.200 mg = 0.72% |
| | | Pluronic F 68 1.000 mg = 0.1% |
| | | Glycerol 20.000 mg = 2.0% |
| | | NaOH or HCl for pH adjustment (pH: 7.0-7.1) |
| | | Water to 1 ml |

TABLE 4

| Sample | Active Ingredient | Inactive ingredient |
|---|---|---|
| FP6 (10000) | 10000 IU EPO | $NaH_2PO_4 \times 2H_2O$ 1.164 mg = 0.1164% |
| | | $Na_2HPO_4 \times 2H_2O$ 2.225 mg = 0.2225% |
| | | NaCl 7.200 mg = 0.72% |
| | | Pluronic F 68 1.000 mg = 0.1% |
| | | Glycerol 20.000 mg = 2.0% |
| | | NaOH or HCl for pH adjustment (pH: 7.0-7.1) |
| | | Water to 1 ml |

Quality of Substances:
Epoetin: quality as demanded by European Pharmacopoeia (Ph. Eur. quality),
Pluronic F68, Sorbitol, Glycerol, NaCl, $Na_2HPO_4 \times 2H_2O$, $NaH_2PO_4 \times 2H_2O$, NaOH, water for injection: Ph. Eur. quality.

Preparation of Pharmaceutical Composition which Comprises EPO

Preparation of placebo solution with Pluronic F68: In the water for injection at room temperature among mixing on the magnetic stirrer buffer ($Na_2HPO_4 \times 2H_2O$, $NaH_2PO_4 \times 2H_2O$) was firstly dissolved then NaCl, one of the polyoly (glycerol or sorbitol) and at last the stabilizing agent Pluronic F68 was added. pH was then adjusted with 1 M NaOH to 7.0-7.1. A clear and colourless solution was obtained.

Preparation of EPO solution: The calculated volume of the EPO solution (calculations were performed regarding the EPO activity) was added to the placebo solution. Just before this step the same volume of placebo solution was taken out. The solution was stirred by using a magnetic stirrer at low rounds. A clear colourless solution was obtained.

The solutions of pharmaceutical compositions comprising EPO at both concentrations were then aseptically (air cleanliness level of class 100) sterile filtered through membrane filter with PVDF (Polyvinylidenefluoride) membrane, pore size 0.2 μm, and 0.8 ml of the filtered solutions were filled in 2 ml vials (vials from the colourless tubular glass hydrolytic type 1) washed and sterilised, and closed with elastic closures from brombutyl rubber, and sealed with aluminium caps.

The invention claimed is:

1. A stable pharmaceutical composition of erythropoietin (EPO), wherein the composition consists of:
   a. a therapeutically effective amount of EPO,
   b. a pharmaceutically acceptable pH buffering system,
   c. a poloxamer polyol,
   d. a polyhydric alcohol and, optionally,
   e. an isotonifying agent.

2. The composition according to claim 1, wherein the composition is aqueous.

3. The composition according to claim 1, wherein the EPO is formulated to provide a quantity per dose in the range of about 500 to 100000 IU EPO.

4. The composition of claim 3, wherein the EPO is formulated to provide a quantity per dose selected from the group consisting of about 1000 IU, about 2000 IU, about 3000 IU, about 4000 IU, about 10000 IU, about 20000 IU, about 25000 IU, about 40000IU, about 50000 IU, about 60000 IU and about 100000 IU.

5. The composition of claim 1, wherein the pH buffering system provides a pH range from about 6 to about 8.

6. The composition of claim 5, wherein the pH buffering system provides a pH range from about 6.8 to about 7.5.

7. The composition of claim 5, wherein the pH buffering system provides a pH of about 7.0.

8. The composition of claim 1, wherein the pH buffering system is a phosphate buffer.

9. The composition of claim 1, wherein the poloxamer polyol is a polyol selected from the group of non-ionic surface active agents.

10. The composition of claim 9, wherein the poloxamer polyol is Pluronic F68.

11. The composition of claim 9, wherein the poloxamer polyol is present in an amount ranging from about 0.05w/v % to about 0.5 w/v %.

12. The composition of claim 9, wherein the poloxamer polyol is present in an about 0.1% w/v.

13. The composition of claim 1, wherein polyhydric alcohol is an alcohol selected from the group comprising glycerol, sorbitol, mannitol and xylitol.

14. The composition of claim 13, wherein the polyhydric alcohol is glycerol.

15. The composition of claim 13, wherein the concentration of polyhydric alcohol is in the range of about 0.1 w/v % to about 10 w/v %.

16. The composition of claim 13, wherein the concentration of polyhydric alcohol is in the range of about 2 w/v % to about 5 w/v %.

17. The composition of claim 1, wherein said isotonifying agent is an inorganic salt.

18. The composition of claim 17, wherein said isotonifying agent is NaCl.

* * * * *

UNITED STATES PATENT AND TRADEMARK OFFICE
CERTIFICATE OF CORRECTION

| | | |
|---|---|---|
| PATENT NO. | : 7,534,870 B2 | Page 1 of 1 |
| APPLICATION NO. | : 10/521298 | |
| DATED | : May 19, 2009 | |
| INVENTOR(S) | : Andreja Vukmirovic et al. | |

It is certified that error appears in the above-identified patent and that said Letters Patent is hereby corrected as shown below:

Column 2, lines 18-22, please delete the following sentences:

"The present invention provides a new stable pharmaceutical composition comprising EPO in according with claim 1. Preferred embodiments are set forth in the sub-claims. The present invention also provides a process according to claim 21, and a use according to claim 22."

In its place, please insert the following sentence:

-- The present invention provides a new stable pharmaceutical composition of erythropoietin (EPO) stabilized with, among other things, a combination of a poloxamer polyol and a polyhydric alcohol. --.

Column 7, line 56, "weighVvolume" should be -- weight/volume --; and
Column 12, line 36, "polyoly" should be -- polyol --.
Column 12, Claim 3, line 67, add -- about -- before "100000 IU EPO."
Column 14, Claim 12, line 5, add -- amount of -- before "about 0.1%. w/v."; and
Column 14, Claim 13, line 7, change "comprising" to -- consisting of --.

Signed and Sealed this

Sixth Day of April, 2010

David J. Kappos
*Director of the United States Patent and Trademark Office*